(12) United States Patent
Loch et al.

(10) Patent No.: US 7,303,622 B2
(45) Date of Patent: Dec. 4, 2007

(54) LUSTROUS BLACK INTERFERENCE PIGMENTS

(75) Inventors: Manuela Loch, Klein-Gerau (DE); Nicole Schupp, Gross-Bieberau (DE); Ralf Anselmann, Luedinghausen-Seppenrade (DE); Lilia Heider, Winchester (GB)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 10/954,359

(22) Filed: Oct. 1, 2004

(65) Prior Publication Data

US 2006/0070552 A1   Apr. 6, 2006

(30) Foreign Application Priority Data

Oct. 1, 2003  (DE) ................. 103 46 167

(51) Int. Cl.
*C09D 5/36*   (2006.01)
(52) U.S. Cl. .............. 106/415; 106/418; 106/456; 106/459
(58) Field of Classification Search ............... 106/418, 106/431, 456, 459; 428/403, 404
See application file for complete search history.

(56) References Cited

U.S. PATENT DOCUMENTS

| | | | |
|---|---|---|---|
| 4,867,793 A * | 9/1989 | Franz et al. ................. 106/415 |
| 6,579,355 B1 * | 6/2003 | Schmidt et al. ............. 106/415 |
| 6,706,330 B2 | 3/2004 | Takahashi et al. | |
| 6,719,838 B2 * | 4/2004 | Heider et al. ............... 106/417 |
| 6,758,894 B1 | 7/2004 | Houmes | |
| 2003/0097965 A1 * | 5/2003 | Heider et al. ............... 106/401 |
| 2004/0123778 A1 * | 7/2004 | Bagala, Sr. ................. 106/415 |
| 2005/0147724 A1 * | 7/2005 | Schweinfurth ............. 426/540 |
| 2006/0051304 A1 * | 3/2006 | Peng et al. .................. 424/59 |

FOREIGN PATENT DOCUMENTS

| EP | 1375604 A1 * | 1/2004 |
|---|---|---|
| JP | 07-331109 | * 12/1995 |
| WO | WO 2004/035693 A1 | 4/2004 |

OTHER PUBLICATIONS

U.S. Appl. No. 60/606,503.*
Maisch, "New effect pigments from grey to black", process in Organic Coatings, 22 (1993), pp. 261-272.*
"New Effect Pigments From Grey To Black", Progress in Organic Coatings, 22 (1993) 261-272, XP000522447.

* cited by examiner

Primary Examiner—C. Melissa Koslow
(74) Attorney, Agent, or Firm—Millen, White, Zelano & Branigan, P.C.

(57) ABSTRACT

The present invention relates to lustrous black interference pigments based on a substrate mixture, characterised in that it has
  (A) a coating of $Fe_3O_4$
  (B) a colorless coating consisting of one or more layers each having a refractive index of $n \leq 1.8$,
  (C) optionally a coating with an absorbent, high-refractive-index material which only covers part of the surface,
and optionally
  (D) an outer protective layer,
and to the use thereof in paints, coatings, powder coatings, printing inks, plastics, ceramic materials, glasses, for the laser marking of papers and plastics, in cosmetic formulations and for the preparation of pigment compositions and dry preparations.

19 Claims, No Drawings

LUSTROUS BLACK INTERFERENCE PIGMENTS

The present invention relates to lustrous black interference pigments based on a substrate mixture which has high- and low-refractive-index layers, and to the use thereof in paints, coatings, powder coatings, printing inks, plastics, ceramic materials, glasses, in cosmetic formulations, for laser marking and for the preparation of pigment compositions and dry preparations.

Lustre or effect pigments are employed in many areas of industry, in particular in the area of automotive paints, decorative coatings, in plastics, in paints, printing inks and in cosmetic formulations.

Black pigments are in many cases based on carbon. Pigments of this type are disclosed, for example, in DE 42 27 082 A1, DE 36 36 076 A1, DE 36 17 430 A1, and EP 0 246 523.B1. The black lustre pigments are prepared either through the use of carbon black, through decomposition processes of organic compounds or.by temperature-dependent calcination of hydrocarbons.

The black lustre pigments known from the prior art have the disadvantage that they are distinguished by a dull lustre and a grey-black or brown-black colour.

EP 0 753 545 B1 discloses goniochromatic lustre pigments based on multicoated, high-refractive-index, nonmetallic, flake-form substrates which are at least partially transparent to visible light and are coated with absorbent, high-refractive-index metal oxides, such as iron oxides and chromium oxides, ilmenite or mixtures of these oxides and which have at least one layer package comprising a colourless, low-refractive-index coating and a reflective, selectively or nonselectively absorbent coating. The lustre pigments known from the prior art exhibit interference colours which are very highly dependent on the viewing angle, which is undesired in the majority of applications. Furthermore, these pigments are in some cases very difficult to prepare or reproduce.

The object of the present invention is therefore to find an inorganic pigment which has a lustrous pure black and at the same time is distinguished by high hiding power and good processing properties and does not have pronounced goniochromaticity.

Surprisingly, black interference pigments having high lustre based on a substrate mixture have now been found which have a certain arrangement of optically functional layers, achieving particular colour and lustre effects. Firstly, defined absorption (absorption layer) is generated on a substrate mixture based on flakes having different particle sizes, and an interference system is subsequently produced thereon using multilayer technology and coating with at least one low-refractive-index, semitransparent layer and optionally an absorbent layer. This combination of absorption and interference produces a final black interference pigment having high lustre and extremely high hiding power.

The black interference pigments according to the invention are distinguished by high blackness (low L value, a and b values are around the zero point) and intense lustre.

The invention thus relates to lustrous black interference pigments based on a substrate mixture, characterised in that it has (A) a coating of $Fe_3O_4$, (B) a colourless coating consisting of one or more layers each having a refractive index of $n \leq 1.8$, (C) optionally a coating with an absorbent, high-refractive-index material which only covers part of the surface, and optionally (D) an outer protective layer.

The invention furthermore relates to the use of the pigments according to the invention in paints, coatings, powder coatings, printing inks, plastics, ceramic materials, glasses and for laser marking. Owing to the high tinting strength and good skin feeling, the non-toxic pigments according to the invention are particularly suitable for decorative cosmetics. Furthermore, the pigments according to the invention can also be used for the preparation of pigment compositions and for the preparation of dry preparations, such as, for example, granules, chips, pellets, briquettes, sausages, etc. The dry preparations can be employed, in particular, in cosmetic formulations, printing inks and surface coatings.

A suitable base substrate for the black pigments according to the invention is a mixture of coarse and fine transparent flake-form substrates. Preferred substrates are phyllosilicates. Particularly suitable are natural and/or synthetic mica, talc, kaolin, flake-form iron oxides, e.g., $Fe_2O_3$, or aluminium oxides, glass flakes, $SiO2$ flakes, $TiO2$ flakes, graphite flakes, synthetic, support-free flakes, BiOCl flakes and other comparable materials.

The size of the base substrates is defined by the target specification of black and lustre intensity or hiding power and must in each case be matched thereto. In general, the flake-form substrates have a thickness of between 0.05 and 5 μm, in particular between 0.1 and 4.5 μm. The size in the other two dimensions is usually from 1 to 200 μm, preferably from 1 to 150 μm and in particular from 1 to 130 μm.

The base substrate is a mixture of identical or different substrates, each having different particle sizes. The substrate mixture can consist of two, three or more different substrates. The substrate mixture preferably consists only of one substrate having two different particle sizes. Preference is furthermore given to substrate mixtures consisting of synthetic mica, $SiO_2$ flakes, $TiO_2$ flakes or glass flakes.

The substrates can be mixed with one another in any ratio. In general, coarse flakes having particle sizes of from 10 to 200 μm, preferably from 40 to 200 μm and in particular from 10 to 130 μm are mixed with fine flakes having particle sizes of from 1 to 60 μm, preferably from 5 to 60 μm and in particular from 10 to 60 μm, before the coating operation. The ratio of fine and coarse substrate particles is preferably chosen for good blackening properties of the pigment having good lustre. Coarse and fine substrates are preferably mixed in the substrate mixture in a ratio of from 10:1 to 1:10, in particular in a ratio of from 5:1 to 1:5. Particular preference is given to 1:1 mixtures. Preferred substrate mixtures consist of mica flakes having different particle sizes. Particularly preferred substrate mixtures consist of coarse and fine flakes, in particular of S-mica (>125 μm) and F-mica (<25 μm).

The thickness of the individual layers on the base substrate is preferably chosen for the optical properties of the pigment. In particular, layer (A) has a strong influence on the colour properties. Layer (B) preferably should be comparatively thin compared with layer (A). For a pigment having high tinting strength, the thicknesses of the individual layers are preferably matched precisely to one another.

The interference pigments according to the invention have a high-refractive-index layer (A) or (C) and a low-refractive-index layer (B) alternating with one another. The high-refractive-index layers (A) and (C) have a refractive index of n>1.8, preferably n>2.0.

The thickness of the $Fe_3O_4$ layer (A) is preferably from 1 to 350 nm, in particular from 50 nm to 300 nm and very particularly preferably from 100 to 250 nm.

Colourless, low-refractive-index materials which are suitable for coating (B) are preferably metal oxides or the corresponding oxide hydrates, such as, for example, $SiO_2$, $Al_2O_3$, AlO(OH), $B_2O_3$, $ZnSiO_4$, $MgF_2$, $MgSiO_3$ or a mixture of the said metal oxides. Layer (B) preferably consists of $SiO_2$, $MgF_2$ or $Al_2O_3$ or mixtures thereof. The low-refractive-index layer (B) can consist of a single low-refractive-index layer or a package of two or more low-refractive-index layers. Layer (B) preferably consists of one or two low-refractive-index layers, which are not identical with respect to the composition, but whose layer thicknesses may be identical or different. Layer (B) preferably consists of an $SiO_2$ layer and/or an $Al_2O_3$ layer.

It is advantageous for the optical properties of the pigments according to the invention if layer (B) is relatively thin. The thickness of layer (B) is, independently of the number of individual layers, from 1 to 350 nm, preferably from 50 to 300 nm and in particular from 20 to 250 nm.

If the final layer applied is the absorbent, high-refractive-index layer (C), this is only present in low concentrations of preferably 2-5% by weight, in particular 2-3% by weight, based on the substrate mixture employed, and thus does not form a continuous layer. Layer (C) preferably consists of $Fe_3O_4$, furthermore of black sulfides, oxynitrides or mixtures thereof. The final layer (C) serves for further optimisation of the lustre.

Coating of the substrates with a high-refractive-index layer (A), a low-refractive-index layer (B) and optionally a further, black, high-refractive-index layer (C) results in the formation of black interference pigments, whose lustre and hiding power can be varied within broad limits.

Particularly preferred interference pigments have the following layer sequences:

substrate mixture+$Fe_3O_4$(A)+$SiO_2$(B)
substrate mixture+$Fe_3O_4$(A)+$SiO_2$(B)+$Al_2O_3$(B)
substrate mixture+$Fe_3O_4$(A)+$SiO_2$(B)+$Fe_3O_4$(C)
substrate mixture+$Fe_3O_4$(A)+$SiO_2$(B)+$Al_2O_3$(B)+$Fe_3O_4$(C)
substrate mixture+$Fe_3O_4$(A)+$Al_2O_3$(B)
substrate mixture+$Fe_3O_4$(A)+$Al_2O_3$(B)+$SiO_2$(B)
substrate mixture+$Fe_3O_4$(A)+$Al_2O_3$(B)+$Fe_3O_4$(C)
substrate mixture+$Fe_3O_4$(A)+$Al_2O_3$(B)+$SiO_2$(B)+$Fe_3O_4$(C)

Combination of absorption and interference in a definable substrate mixture gives a black, lustrous interference pigment having an adjustable colour content. Defined adjustment of the a and b values enables black interference pigments having a gold, green, red or blue tint to be obtained.

The interference pigments according to the invention can be prepared relatively easily through the production of high- and low-refractive-index interference layers of precisely defined thickness and having a smooth surface on the finely divided, flake-form substrates.

The metal-oxide layers are preferably applied by wet-chemical methods, it being possible to use the wet-chemical coating processes developed for the preparation of pearlescent pigments. Processes of this type are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or also in further patent documents and other publications known to the person skilled in the art.

Before the coating operation, the substrate mixture comprising coarse and fine flakes is firstly prepared by simple mixing. In the case of wet coating, the substrate mixture is suspended in water and one or more hydrolysable metal salts are added at a pH which is suitable for hydrolysis, which is selected in such a way that the metal oxides or metal oxide hydrates are precipitated directly onto the flakes without secondary precipitations occurring. The pH is usually kept constant by simultaneous metering-in of a base or acid. The $SiO_2$ layer is generally produced from sodium or potassium water-glass. The pigments are subsequently separated off, washed and dried and calcined in a reducing atmosphere, preferably under forming gas, where the calcination temperature can be optimised with respect to the coating present in each case. In general, the calcination temperatures are between 500 and 900° C. The reduction is preferably carried out in a forming-gas stream having the composition $N_2$ or argon with a concentration of 4-10% of $H_2$, in particular 4-8% and very particularly preferably 8% of $H_2$. In particular, the forming gas employed consists of 92% of $N_2$ and 8% of $H_2$. If desired, the pigments can be separated off, dried and optionally calcined after application of individual coatings and then re-suspended for the precipitation of the further layers. Furthermore, the coating can also be carried out in a fluidised-bed reactor by gas-phase coating, e.g, a CVD or PVD process, it being possible, for example, to use correspondingly the processes proposed in EP 0 045 851 and EP 0 106 235 for the preparation of pearlescent pigments.

The hue of the pigments can be varied within broad limits through the choice of the coating amounts or the layer thicknesses resulting therefrom. The fine tuning for a certain hue can be achieved beyond the pure choice of amount by approaching the desired colour under visual or measurement technology control.

In order to increase the light, water and weather stability, it is frequently advisable to subject the finished pigment to post-coating or post-treatment, depending on the area of application. Suitable post-coatings or post-treatments are, for example, the processes described in German Patent 22 15 191, DE-A 31 51 354, DE-A 32 35 017 or DE-A 33 34 598. This post-coating (layer D) further increases the chemical stability or simplifies handling of the pigment, in particular incorporation into various media. In order to improve the wettability, dispersibility and/or compatibility with the user media, functional coatings of $Al_2O_3$ or $ZrO_2$ or mixtures thereof can be applied to the pigment surface. Also possible are organic post-coatings, for example with silanes, as described, for example, in EP 0090259, EP 0 634 459, WO 99/57204, WO 96/32446, WO 99/57204, U.S. Pat. No. 5,759,255, U.S. Pat. No. 5,571,851, WO 01/92425 or in J. J. Ponjeé, Philips Technical Review, Vol. 44, No. 3, 81 ff. and P. H. Harding J. C. Berg, J. Adhesion Sci. Technol. Vol.11 No. 4, pp. 471-493.

It goes without saying that, for the various applications, the interference pigments according to the invention can also advantageously be used in blends with organic dyes and/or pigments, such as, for example, transparent and opaque white, coloured and black pigments, and with flake-form iron oxides, organic pigments, holographic pigments, LCPs (liquid crystal polymers) and conventional transparent, coloured and black lustre pigments based on metal oxide-coated flakes based on mica, glass, $Al_2O_3$, $Fe_2O_3$ and $SiO_2$, etc. The black interference pigments according to the invention can be mixed in any ratio with commercially available pigments and fillers.

Fillers which may be mentioned are, for example, natural and synthetic mica, nylon powder, pure or filled melamine resins, talk, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions regarding the particle shape of the filler. It can be, for example, flake-shaped, spherical or needle-shaped, in accordance with requirements.

Owing to their good skin adhesion, the pigments according to the invention are particularly suitable for cosmetic formulations, both in the area of decorative cosmetics and for personal-care products. On use of the pigments according to the invention with dyes, carbon black and/or other effect pigments, particularly effective effects can be achieved with them in the various application media, for example in cosmetic formulations, such as, for example, mascara, eyeliner and kohl eye pencil.

The pigments according to the invention can of course also be combined in the formulations with cosmetic raw materials and assistants of any type. These include, inter alia, oils, fats, waxes, film formers, preservatives and assistants which generally determine the technical properties, such as, for example, thickeners and Theological additives, such as, for example, bentonites, hectorites, silicon dioxides, Ca silicates, gelatine, high-molecular-weight carbohydrates and/or surface-active assistants, etc.

The formulations comprising the pigments according to the invention may belong to the lipophilic, hydrophilic or hydrophobic type. In the case of heterogeneous formulations having discrete aqueous and non-aqueous phases, the pigments according to the invention may in each case be present in only one of the two phases or alternatively distributed over both phases.

The pH values of the formulations can be between 1 and 14, preferably between 2 and 11 and particularly preferably between 5 and 8. No limits are set for the concentrations of the interference pigments according to the invention in the formulation. They can be—depending on the application—between 0.001 (rinse-off products, for example shower gels) and 100% (for example lustre-effect articles for particular applications). The pigments according to the invention may furthermore also be combined with cosmetic active ingredients. Suitable active ingredients are, for example, insect repellents, UV A/BC protective filters (for example OMC, B3 and MBC), anti-ageing active ingredients, vitamins and derivatives thereof (for example vitamin A, C, E, etc.), self-tanning agents (for example DHA, erythrulose, inter alia), and further cosmetic active ingredients, such as, for example, bisabolol, LPO, ectoin, emblica, allantoin, bioflavonoids and derivatives thereof.

The pigments according to the invention are furthermore suitable for the preparation of flowable pigment compositions and dry preparations comprising one or more pigments according to the invention, binders and optionally one or more additives. The pigment compositions according to the invention can contain one or more interference pigments according to the invention, binders and optionally additives, water and/or one or more solvents. The term dry preparations is also taken to mean preparations which comprise from 0 to 8% by weight, preferably from 2 to 8% by weight, in particular from 3 to 6% by weight, of water and/or a solvent or solvent mixture. The dry preparations are preferably in the form of pellets, granules, chips, sausages or briquettes and have particle sizes of 0.2-80 mm. The dry preparations are used, in particular, in the production of printing inks and in cosmetic formulations.

The pigments according to the invention are compatible with a multiplicity of colour systems, preferably from the areas of paints, coatings and printing inks. For the production of printing inks, a multiplicity of binders, in particular water-soluble grades, is suitable, as marketed, for example, by BASF, Marabu, Pröll, Sericol, Hartmann, Gebr. Schmidt, Sicpa, Aarberg, Siegberg, GSB-Wahl, Follmann, Ruco or Coates Screen INKS GmbH. The printing inks can be water-based or solvent-based. The pigments are furthermore also suitable for the laser marking of paper and plastics and for applications in the agricultural sector, for example for greenhouse sheeting, and, for example, for the colouring of tent awnings.

The invention furthermore also relates to the use of the pigments in formulations, such as paints, printing inks, security printing inks, surface coatings, powder coatings, plastics, ceramic materials, glasses, in cosmetic formulations, as dopant for the laser marking of papers and plastics and for the preparation of pigment compositions and dry preparations.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

EXAMPLES

Example 1

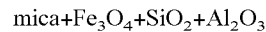

Step 1.1

42 g of S-mica (10-130 µm) and 18 g of F-mica (1-15 µm) are suspended in 1.0 l of deionised water and heated to 80° C. with vigorous stirring. The mica suspension is adjusted to pH=2.8 using 10% sulfuric acid. 46.05 g of iron(II) sulfate and 503.49 g of iron(III) chloride solution ($w_{Fe}$=15%) are metered into this suspension, during which the pH is kept constant using sodium hydroxide solution (32%). Colour measurements are carried out during the coating operation. The metering of the iron(III) chloride solution is interrupted as soon as the hue angle has reached 56° and 59°. The suspension is stirred at 80° C. for a further 60 minutes, and the pH is adjusted to pH=7 using sodium hydroxide solution (w=32%). 266.52 g of sodium water-glass solution (prepared from 133.26 g of sodium water-glass ($w_{SiO2}$=27%) and 133.26 g of deionised water) are subsequently metered in, during which the pH is kept constant at pH=7.0 using 10% hydrochloric acid. After addition of the precipitation solution, the mixture is stirred for a further 30 minutes. Finally, 96.64 g of aluminium sulfate solution (prepared from 24.16 g of aluminium sulfate heptahydrate in 72.48 g of deionised water) are metered in, during which the pH is kept constant using 32% sodium hydroxide solution. The suspension is stirred at 80° C. for 30 minutes. For work-up, the pigment is filtered off, washed with deionised water, dried at 110° C. and calcined for 30 minutes at 575° C. under a forming-gas atmosphere (8% of $H_2$/92% of $N_2$).

Interference pigments having an intensely black lustre and the following colour values are obtained (Minolta CR 300 calorimeter):

| | |
|---|---|
| L value: | 30 → 32 |
| a value: | 0 → 1 |
| b value: | −2 → −4 |
| C value (chroma): | 2 → 4 |

Example 2 mica+$Fe_3O_4$+$SiO_2$+$Fe_3O_4$ 50 g of N-mica (10-60 μm) and 50 g of F-mica (1-15 μm) are suspended in 1.2 l of deionised water and heated to 80° C. with vigorous stirring. The mica suspension is adjusted to pH=3.2 using 10% hydrochloric acid. 153.05 g of iron(III) chloride solution ($w_{Fe}$=15%) diluted with 612.2 g of deionised water are metered into this suspension, during which the pH is kept constant using sodium hydroxide solution (32%). Colour measurements are carried out during the coating operation. The suspension is stirred at 80° C. for a further 30 minutes, and the pH is adjusted to pH=7.0 using sodium hydroxide solution (w=32%). 290 g of sodium water-glass solution (prepared from 145 g of sodium water-glass ($w_{SiO2}$=27%) and 145 g of deionised water) are subsequently metered in, during which the pH is kept constant at pH=7.0 using 10% hydrochloric acid. After addition of the precipitation solution, the mixture is stirred for a further 30 minutes. Finally, 65.40 g of iron(III) chloride solution ($w_{Fe}$)=15%) are metered in at pH 3.2, during which the pH is kept constant using 32% sodium hydroxide solution. The suspension is stirred at 80° C. for 30 minutes and adjusted to pH 7.0 using NaOH (32%). For work-up, the pigment is filtered off, washed with deionised water, dried at 110° C. and calcined for 30 minutes at 575° C. under a forming-gas atmosphere (8% of $H_2$/92% of $N_2$).

Interference pigments having an intensely black lustre and the following colour values are obtained (Minolta CR 300 calorimeter):

| | |
|---|---|
| L value: | 36 → 38 |
| a value: | −1 → 0 |
| b value: | −9 → −6 |
| C value (chroma): | 9 → 6 |

Use Examples

Example A

Creme Mascara (O/W)

| | |
|---|---|
| Phase A: | 15% of interference pigment from Example 2 |
| Phase B: | 8% of stearic acid (1) |
| | 6% of beeswax (1) |
| | 4% of carnauba wax (2) |
| | 3% of Eutanol (3) |
| | 2% of Arlacel 83 V (4) |
| | 0.1% of propylparaben (1) |
| | 0.5% of tocopherol acetate (1) |
| Phase C: | 50.84% of water |
| | 2.3% of triethanolamine (1) |
| | 8% of shellac (5) |
| | 0.25% of methylparaben (1) |
| | 0.01% of biotin (1) |

Preparation:

Melt all constituents of phase B together at about 80° C., stir until everything has melted. Stir in the interference pigments of phase A. Dissolve the shellac of phase C in the water, warm to 75° C. Add the remaining constituents of phase C and dissolve. At 75° C., slowly add phase C to phase A/B with stirring, homogenise for 2 minutes. Cool the mass to room temperature with stirring.

Sources of Supply:
(1) Merck KGaA
(2) Kahl & Co
(3) Cognis GmbH
(4) Uniqema
(5) Paroxite Ltd.

Example B

Eyeliner

| | |
|---|---|
| Phase A: | 20% of interference pigment from Example 1 |
| | 2% of Ronasphere ® (1) |
| | 0.4% of Carpobol EDT 2001 (2) |
| | q.s. citric acid (1) |
| | to 60% of water |
| Phase B: | 4.0% of glycerol, anhydrous (1) |
| | 0.9% of triethanolamine (1) |
| | 2.0% of Luviskol VA 64 powder (3) |
| | 1.0% of Germaben II (4) |
| | 9.7% of water |

Preparation:

Disperse the interference pigment and Ronasphere® in the water of phase A. Acidify with a few drops of citric acid in order to reduce the viscosity, scatter in Carpobol EDT with stirring. After complete dissolution, slowly stir in the pre-dissolved phase B and adjust the pH to 7.0-7.5.

Sources of Supply:
(1) Merck KGaA
(2) Noveon
(3) BASF AG
(4) ISP Global Technologies The preceding examples can be repeated with similar success by substituting the generically or specifically described reactants and/or operating conditions of this invention for those used in the preceding examples.

The entire disclosures of all applications, patents and publications, cited herein and of corresponding German application No.10346167.1, filed Oct. 1, 2003 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Lustrous black interference pigments comprising a mixture of different substrates having
   (A) a coating of $Fe_3O_4$,
   (B) a colorless coating consisting of one or more layers each having a refractive index of n<1.8,
   (C) a coating with an absorbent, high-refractive-index material which contains $Fe_3O_4$, a black sulfide, a black oxynitride or a mixture thereof, and which only covers part of the underlying surface, and
   (D) optionally an outer protective layer.

2. Lustrous black interference pigments according to claim 1, wherein the mixture of different substrates contains flakes having different particle sizes.

3. Lustrous black interference pigments according to claim 1, wherein the flakes are natural mica, synthetic mica, BiOCl flakes, glass flakes, $Fe_2O_3$ flakes, graphite flakes, $Al_2O_3$ flakes, $SiO_2$ flakes, or $TiO_2$ flakes, or a mixture thereof.

4. Lustrous black interference pigments according to claim 1, wherein the mixture of different substrates contains identical flakes which differ in particle size.

5. Lustrous black interference pigments according to claim 1, wherein layer (B) contains $SiO_2$, $Al_2O_3$, AlO(OH), $B_2O_3$, $ZnSiO_4$, $MgF_2$, $MgSiO_3$ or a mixture thereof.

6. Lustrous black interference pigments according to claim 1, wherein layer (A) has a thickness of 1 to 350 nm.

7. Lustrous black interference pigments according to claim 1, wherein layer (B) has a thickness of 10 to 250 nm.

8. Lustrous black interference pigments according to claim 1, wherein layer (C) consists of $Fe_3O_4$.

9. Lustrous black interference pigments according to claim 1, wherein the substrate mixture contains particles of 10 to 200 μm and 1 to 60 μm in a ratio of 10:1 to 1:10.

10. Lustrous black interference pigments according to claim 9, wherein said ratio is 5:1 to 1:5.

11. Lustrous black interference pigments according to claim 9, wherein said ratio is 1:1.

12. Lustrous black interference pigments according to claim 9, wherein the mixture of different substrates contains a substrate having particles of 40 to 200 μm and a substrate having particles of 5 to 60 μm mixed together.

13. Lustrous black interference pigments according to claim 9, wherein the mixture of different substrates contains a substrate having particles of 10 to 130 μm and a substrate having particles of 10 to 60 μm mixed together.

14. Lustrous black interference pigments according to claim 9, wherein the mixture of different substrates consists essentially of mica flakes.

15. A dry preparation in the form of pellets, granules, chips, or briquettes comprising interference pigments according to claim 1.

16. A dry preparation in the form of pellets, granules, chips, briquettes or sausages comprising interference pigments according to claim 1.

17. A pigment composition or dry preparation comprising interference pigments according to claim 1, a binder and optionally an additive, water and/or one or more solvents.

18. A paint, coating, powder coating, printing ink, plastic, ceramic material, glass, cosmetic formulation, laser marking, pigment composition or dry preparation comprising lustrous black interference pigments according to claim 1.

19. A process for the preparation of the lustrous black interference pigments according to claim 1, comprising coating the mixture of different substrates by a wet-chemical method, by a CVD or PVD process.

* * * * *